United States Patent
Auzias et al.

(10) Patent No.: US 10,662,330 B2
(45) Date of Patent: May 26, 2020

(54) SILICONE COMPOSITION CROSSLINKABLE TO GIVE SILICONE GEL

(71) Applicant: Wacker Chemie AG, Munich (DE)

(72) Inventors: Birgit Auzias, Emmerting (DE); Brigitte Hergert, Burghausen (DE); Arvid Kuhn, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 29 days.

(21) Appl. No.: 16/072,738

(22) PCT Filed: Jan. 16, 2017

(86) PCT No.: PCT/EP2017/050758
§ 371 (c)(1),
(2) Date: Jul. 25, 2018

(87) PCT Pub. No.: WO2017/129429
PCT Pub. Date: Aug. 3, 2017

(65) Prior Publication Data
US 2019/0002696 A1    Jan. 3, 2019

(30) Foreign Application Priority Data
Jan. 29, 2016    (DE) .................. 10 2016 201 363

(51) Int. Cl.
| | | |
|---|---|---|
| C08L 83/04 | (2006.01) | |
| C09J 183/04 | (2006.01) | |
| C08L 83/00 | (2006.01) | |
| C08K 5/56 | (2006.01) | |
| A61L 15/26 | (2006.01) | |
| A61L 15/58 | (2006.01) | |
| A61L 26/00 | (2006.01) | |
| C08G 77/12 | (2006.01) | |
| C08G 77/20 | (2006.01) | |

(52) U.S. Cl.
CPC .............. *C08L 83/04* (2013.01); *A61L 15/26* (2013.01); *A61L 15/58* (2013.01); *A61L 26/008* (2013.01); *A61L 26/0019* (2013.01); *C08K 5/56* (2013.01); *C08L 83/00* (2013.01); *C09J 183/04* (2013.01); *A61L 2430/34* (2013.01); *C08G 77/12* (2013.01); *C08G 77/20* (2013.01); *C08L 2203/02* (2013.01); *C08L 2203/20* (2013.01); *C08L 2205/025* (2013.01); *C08L 2312/08* (2013.01)

(58) Field of Classification Search
CPC ........................... C08L 83/04; C08L 2312/08
See application file for complete search history.

(56) References Cited

U.S. PATENT DOCUMENTS

| | | | | |
|---|---|---|---|---|
| 4,806,391 | A * | 2/1989 | Shorin .................... | B41M 1/30 427/288 |
| 5,679,734 | A | 10/1997 | Peccoux et al. | |
| 8,524,842 | B2 | 9/2013 | Jung et al. | |
| 8,586,191 | B2 | 11/2013 | Lorentz et al. | |
| 2005/0250903 | A1* | 11/2005 | Tanaka ................... | C08L 83/04 524/861 |
| 2010/0086760 | A1* | 4/2010 | Zhu ........................ | B82Y 30/00 428/220 |
| 2011/0098400 | A1* | 4/2011 | Blanc-Magnard ..... | C08G 77/20 524/500 |
| 2015/0132586 | A1* | 5/2015 | Mueller ............... | C09D 183/04 428/447 |
| 2015/0380636 | A1* | 12/2015 | Fujisawa ................. | C08K 3/22 524/783 |

FOREIGN PATENT DOCUMENTS

| | | |
|---|---|---|
| EP | 0322118 A1 | 6/1989 |
| EP | 0737721 A1 | 10/1996 |
| EP | 1633830 B1 | 8/2007 |
| EP | 2395053 A1 | 12/2011 |
| EP | 2608813 B1 | 8/2014 |
| JP | 2005344106 A | 12/2005 |
| WO | 2008057155 A1 | 5/2008 |
| WO | WO-2013160081 A1 * | 10/2013 |

* cited by examiner

*Primary Examiner* — Robert C Boyle
(74) *Attorney, Agent, or Firm* — Brooks Kushman P.C.

(57) ABSTRACT

Highly adhesive, soft silicone gels are prepared from an aliphatically unsaturated organopolysiloxanes and an organosilicon compound crosslinker of high molecular weight and a very low silicon-bonded hydrogen content.

10 Claims, No Drawings

SILICONE COMPOSITION CROSSLINKABLE TO GIVE SILICONE GEL

CROSS REFERENCE TO RELATED APPLICATIONS

This application is the U.S. National Phase of PCT Appln. No. PCT/EP2017/050758 filed Jan. 16, 2017, which claims priority to German Application No. 10 2016 201 363.7 filed Jan. 29, 2016, the disclosures of which are incorporated in their entirety by reference herein.

BACKGROUND OF THE INVENTION

1. Field of the Invention

The invention relates to a silicone composition crosslinkable to afford silicone gels from a crosslinker of very low SiH density and relatively long chain length.

2. Description of the Related Art

Silicone gels are established in medicine as wound adhesives. There is a need for products having relatively high adhesive force coupled with residue-free detachment behavior.

It is common knowledge that the adhesive force of a silicone gel may be adjusted via the hardness thereof. The softer the gel, the higher the adhesive force. Here, the softness is usually achieved via a low crosslinking density. However, one limitation is that adjustment to excessive softness results in cohesion failure and thus in residue formation on the skin.

Known silicone formulations for gels having adhesive properties for applications on the skin vary for example in terms of number of SiH groups per molecule in the SiH crosslinker, viscosity of the SiH crosslinker, arrangement of the SiH groups in the SiH crosslinker, SiH group/vinyl group ratio, and SiH content in the SiH crosslinker. Such silicone formulations are described for example in EP 0737721 A, EP 2608813 A, EP 322118 A, EP 1633830 A and WO 08057155.

WO 08057155 discloses silicone formulations for gels which contain as chain extenders not only short-chain SiH crosslinkers but also crosslinkers comprising long-chain terminal SiH groups. The SiH/vinyl ratio is 0.7 to 1.5 and the ratio of the SiH groups in the chain extender to all SiH groups is 0.4 to 1.0. The content of hydrogen groups in the SiH crosslinkers is in the range from 0.03% by weight to 1.44% by weight.

SUMMARY OF THE INVENTION

The invention provides a silicone composition (S) crosslinkable to afford silicone gels containing
(A) polyorganosiloxane(s) containing at least two alkenyl groups per molecule, having a viscosity at 25° C. of 200 to 500,000 mPa·s,
(B) organosilicon compound containing at least two SiH groups per molecule having an average content of 2.5 to 3.5 SiH groups per molecule and a content of not more than 0.025% by weight of hydrogen in the SiH groups, and
(C) a hydrosilylation catalyst.

DETAILED DESCRIPTION OF THE PREFERRED EMBODIMENTS

It has now been found that, surprisingly, in the silicone composition (S), use of an organosilicon compound (B) as a crosslinker, having a very low SiH density and a relatively long chain length, results in markedly improved adhesion properties of the crosslinked silicone gels. It was previously thought that the organosilicon compound (B) in the formulation would result in a very low network density and thus unacceptably soft formulations.

The alkenyl-containing polyorganosiloxane (A) is preferably constructed from units of general formula (1)

$$R^1_x R^2_y SiO_{(4-x-y)/2} \quad (1),$$

in which
$R^1$ represents a monovalent, unsubstituted or halogen- or cyano-substituted, $C_1$-$C_{10}$-hydrocarbon radical optionally bonded to silicon via an organic divalent group and containing at least one aliphatic carbon-carbon multiple bond,
$R^2$ represents a monovalent, unsubstituted or halogen- or cyano-substituted, SiC-bonded $C_1$-$C_{10}$-hydrocarbon radical free from aliphatic carbon-carbon multiple bonds
x is 0, 1 or 2,
y is 0, 1, 2 or 3,
with the proviso that at least two radicals $R^1$ are present in each molecule and the average value of (x+y) is in the range from 1.8 to 2.5.

The alkenyl groups $R^1$ participate in an addition reaction with the SiH-functional organosilicon compound (B). Typically employed are alkenyl groups having 2 to 6 carbon atoms, such as vinyl, allyl, methallyl, 1-propenyl, 5-hexenyl, ethynyl, butadienyl, hexadienyl, cyclopentenyl, cyclopentadienyl, and cyclohexenyl, preferably vinyl and allyl.

Organic divalent groups by means of which the alkenyl groups $R^1$ may be bonded to silicon of the polymer chain are composed of for example oxyalkylene units, such as those of general formula formula (2)

$$-(O)_m[(CH_2)_n O]_o- \quad (2),$$

in which
m is 0 or 1, in particular 0,
n is 1 to 4, in particular 1 or 2 and
o is 1 to 20, in particular 1 to 5.

The oxyalkylene units of general formula (2) are bonded to a silicon atom on the left hand side.

The radicals $R^1$ may be bonded in any position of the polymer chain, in particular at the terminal silicon atoms.

Examples of unsubstituted radicals $R^2$ are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical; cycloalkyl radicals such as cyclopentyl, cyclohexyl, 4-ethylcyclohexyl, cycloheptyl radicals, norbornyl radicals and methylcyclohexyl radicals; aryl radicals such as the phenyl, biphenylyl, and naphthyl radicals; alkaryl radicals such as o-, m-, p-tolyl radicals and ethylphenyl radicals; and aralkyl radicals, such as the benzyl radical and the alpha- and the ß-phenylethyl radicals.

Examples of substituted hydrocarbons as radicals $R^2$ are halogenated hydrocarbons such as the chloromethyl, 3-chloropropyl, 3-bromopropyl, 3,3,3-trifluoropropyl and 5,5,5,4,4,3,3-heptafluoropentyl radicals and the chlorophenyl-, dichlorophenyl- and trifluorotolyl radicals.

$R^2$ preferably has 1 to 6 carbon atoms. Methyl and phenyl are especially preferred.

Polyorganosiloxane (A) may also be a mixture of different alkenyl-containing polyorganosiloxanes differing for example in the alkenyl group content, the type of alkenyl group or structurally.

The structure of the alkenyl-containing polyorganosiloxanes (A) may be linear, cyclic or branched. The content of tri- and/or tetrafunctional units which result in branched polyorganosiloxanes is typically very low, preferably less than 20 mol %, in particular not more than 0.1 mol %.

Particular preference is given to the use of vinyl-containing polydimethylsiloxanes of general formula (3)

$$(ViMe_2SiO_{1/2})_2(ViMeSiO)_p(Me_2SiO)_q \qquad (3),$$

wherein
Vi represents a vinyl radical and
Me represents a methyl radical
and the non-negative integers p and q conform to the following relations: $p \geq 0$, $50 < (p+q) < 20{,}000$, preferably $100 < (p+q) < 1500$, and $0 < (p+1)/(p+q) < 0.2$. In particular, $p=0$.

The viscosity of the polyorganosiloxane (A) at 25° C. is preferably 300 to 200,000 mPa·s, in particular 800 to 150,000 mPa·s.

In a preferred embodiment a portion of the polyorganosiloxane (A) is composed of organosiloxane resin(s) (A1) constructed from units of general formulae I, II, III and IV $$R_3SiO_{1/2} \qquad (I),$$

$$R_2SiO_{2/2} \qquad (II),$$

$$RSiO_{3/2} \qquad (III),$$

$$SiO_{4/2} \qquad (IV),$$

in which
R is selected from $R^1$, $R^2$ and OH,
with the proviso that
  at least 20 mol % of the units are selected from units of general formulae III and IV,
  at least 2 of the radicals R are radicals $R^1$ and not more than 2% by weight of the radicals R are radicals OH.

Preferably not more than 20% by weight, in particular not more than 10% by weight, of the polyorganosiloxanepolyorganosiloxane(s) (A) are composed of organosiloxane resin (A1).

The preferred radicals R are methyl, phenyl and vinyl.

The organosiloxane resins (A1) preferably contain at least 30 mol %, in particular at least 40 mol %, and preferably not more than 80 mol %, in particular not more than 70 mol %, of units of general formulae III and IV.

The organosiloxane resins (A1) are preferably MQ silicone resins (MQ) containing at least 80 mol % of units, preferably at least 95 mol %, in particular at least 97 mol % of units, of general formulae I and IV. The average ratio of units of general formulae I to IV is preferably at least 0.25, in particular at least 0.5, and preferably not more than 2, in particular not more than 1.5.

Preferably not more than 1% by weight, in particular not more than 0.5% by weight of the radicals R, are radicals OH.

Preferably at least 0.01% by weight, more preferably at least 0.05% by weight, and preferably not more than 8 mol %, in particular not more than 5 mol %, of the radicals R are radicals $R^1$.

The average molecular weight Mn of the organosiloxane resins (A1) is preferably at least 200 g/mol, in particular at least 1000 g/mol, and preferably not more than 100,000 g/mol, in particular not more than 20,000 g/mol.

The organosilicon compound (B) containing at least two SiH functions per molecule is preferably constructed from units of general formula (4)

$$H_a R^3_b SiO_{(4-a-b)/2} \qquad (4),$$

in which
$R^3$ represents a monovalent, unsubstituted or halogen- or cyano-substituted, SiC-bonded $C_1$-$C_{18}$-hydrocarbon radical free from aliphatic carbon-carbon multiple bonds and
a is 0, 1, or 2,
b is 0, 1, 2 or 3,
with the proviso that at least two silicon-bonded hydrogen atoms per molecule are present.

Examples of $R^3$ are the radicals recited for $R^2$. $R^3$ preferably has 1 to 6 carbon atoms. Methyl and phenyl are especially preferred.

The hydrogen content of the organosilicon compound (B) in the SiH groups relates exclusively to the hydrogen atoms bonded directly to silicon atoms. It is preferably in the range from 0.002% to 0.02% by weight of hydrogen, preferably from 0.005 to 0.018% by weight of hydrogen. The hydrogen content may be determined with $^1$H NMR.

The organosilicon compound (B) preferably contains at least 50 and not more than 1000 silicon atoms per molecule. The use of organosilicon compound (B) containing 100 to 700 silicon atoms per molecule is preferred.

The organosilicon compound (B) preferably contains on average from 2.6 to 3.4 SiH groups, in particular 2.6 to 3.3 SiH groups, per molecule. In a particularly preferred embodiment the organosilicon compound (B) contains 2.6 to 2.9 SiH groups per molecule.

The viscosity of the organosilicon compound (B) at 25° C. is preferably 500 to 20,000 mPa·s, in particular 1000 to 10,000 mPa·s.

The structure of the organosilicon compound (B) may be linear, branched, cyclic or networklike.

Particularly preferred organosilicon compounds (B) are linear polyorganosiloxanes of general formula (5)

$$(HR^4_2SiO_{1/2})_c(R^4_3SiO_{1/2})_d(HR^4SiO_{2/2})_e(R^4_2SiO_{2/2})_f \qquad (5),$$

wherein
$R^4$ has the same definitions as $R^3$ and
the non-negative integers c, d, e and f fulfill the following relations: $(c+d)=2$, $(c+e) \geq 2$ and $50 < (e+f) < 1000$.

It is preferable to employ 2 to 50, in particular 5 to 40, parts by weight of organosilicon compound (B) per 100 parts by weight of polyorganosiloxane (A).

Employable as hydrosilylation catalyst (C) are all known catalysts which catalyze the hydrosilylation reactions that take place during the crosslinking of addition-crosslinking silicone compositions.

As hydrosilylation catalysts (C) in particular metals and compounds thereof from the group of platinum, rhodium, palladium, ruthenium and iridium are employed.

It is preferable to employ platinum and platinum compounds. Particularly preferred are platinum compounds soluble in polyorganosiloxanes. Employable as soluble platinum compounds are for example the platinum-olefin complexes of formulae $(PtCl_2.olefin)_2$ and $H(PtCl_3.olefin)$, wherein alkenes having 2 to 8 carbon atoms, such as ethylene, propylene, isomers of butene and octene, or cycloalkenes having 5 to 7 carbon atoms, such as cyclopentene, cyclohexene and cycloheptene, are preferably employed. Further soluble platinum catalysts are the platinum cyclopropane complex of formula $(PtCl_2C_3H_6)_2$, the reaction products of hexachloroplatinic acid with alcohols, ethers and aldehydes or mixtures thereof or the reaction product of hexachloroplatinic acid with methylvinylcyclotetrasiloxane in the presence of sodium bicarbonate in ethanolic solution. Complexes of platinum with vinyl siloxanes, such as sym-divinyltetramethyldisiloxane, are particularly preferred.

The hydrosilylation catalyst (C) may be employed in any desired form, including for example in the form of hydrosilylation catalyst-containing microcapsules or polyorganosiloxane particles.

The content of hydrosilylation catalyst (C) is preferably chosen such that the silicone composition (S) has a Pt content of 0.1 to 200 ppmw, in particular of 0.5 to 40 ppmw.

The silicone composition (S) may contain one or more fillers (D). Non-reinforcing fillers (D) having a BET surface area of up to 50 $m^2$/gram are for example quartz, diatomaceous earth, calcium silicate, zirconium silicate, zeolites, metal oxide powders, such as aluminum, titanium, iron or zinc oxides or mixed oxides thereof, barium sulfate, calcium carbonate, gypsum, silicon nitride, silicon carbide, boron nitride, glass powder and plastics powder. Reinforcing fillers, i.e. fillers having a BET surface area of at least 50 $m^2$/g, in particular 100 to 400 $m^2$/g, are for example pyrogenic silica, precipitated silica, aluminum hydroxide, carbon black, such as furnace black and acetylene black, and silicon-aluminum mixed oxides of large BET surface area.

The recited fillers (D) may be hydrophobized, for example as a result of treatment with organosilanes, organosilazanes and/or organosiloxanes, or due to etherification of hydroxyl groups to alkoxy groups. One type of filler (D) may be used; a mixture of two or more fillers (D) may also be used.

The silicone compositions (S) preferably comprise 0% by weight, more preferably at least 5% by weight, and in particular at least 10% by weight and not more than 20% by weight, of filler fraction (D).

In one preferred embodiment the silicone composition (S) contains not only the SiH-functional organosilicon compound (B) but also a linear polydiorganosiloxane (E) whose two chain ends each contain an SiH group and whose chain is free from SiH groups. The polydiorganosiloxane (E) preferably serves as a chain extender.

The polydiorganosiloxane (E) preferably contains not only the SiH groups but also exclusively monovalent, unsubstituted or halogen- or cyano-substituted, $C_1$-$C_{10}$-hydrocarbons free from aliphatic carbon-carbon multiple bonds, more preferably $C_1$-$C_6$-hydrocarbon radicals, and in particular, methyl radicals.

The polydiorganosiloxane (E) preferably contains at least 50 and not more than 800 silicon atoms per molecule. The use of polydiorganosiloxane (E) containing 100 to 700 silicon atoms per molecule is preferred.

The viscosity of the organosilicon compound (B) at 25° C. is preferably 200 to 10,000 mPa·s, in particular 500 to 3000 mPa·s.

Per 100 parts by weight of the SiH-functional organosilicon compound (B), the silicone composition (S) preferably contains 0 to 200 parts by weight, in particular 50 to 150 parts by weight, of polydiorganosiloxane (E).

Particularly good adhesion properties are achieved when the SiH-functional organosilicon compound (B) and optionally polydiorganosiloxane (E) are present in the crosslinkable silicone composition in amounts such that the molar ratio of all SiH groups of the organosilicon compounds (B) and optionally polydiorganosiloxane (E) to all alkenyl groups in the silicone composition (S) is 0.3 to 0.7, in particular 0.35 to 0.65.

The silicone composition (S) may as desired contain as a further constituent (Z) possible additives in a proportion of 0% to 70% by weight, preferably 0.0001% to 40% by weight. These additives may be, for example, resin-like polyorganosiloxanes distinct from the polyorganosiloxanes (A) and (B), adhesion promoters, pigments, dyes, plasticizers, organic polymers, heat stabilizers and inhibitors. These include additives, such as colorants, pigments and active pharmaceutical ingredients. Also includable as a constituent are thixotropizing constituents, such as highly disperse silica or other commercially available thixotropic additives. Also includable as a further constituent (Z) for better crosslinking is preferably not more than 0.5% by weight, more preferably not more than 0.3% by weight, and in particular <0.1% by weight, of peroxide.

Examples of employable solvents (L) are ethers, in particular aliphatic ethers such as dimethyl ether, diethyl ether, methyl t-butyl ether, diisopropyl ether, dioxane or tetrahydrofuran; esters, in particular aliphatic esters such as ethyl acetate or butyl acetate, ketones, in particular aliphatic ketones such as acetone or methyl ethyl ketone; sterically hindered alcohols, in particular aliphatic alcohols such as i-propanol and t-butanol; amides such as DMF; aromatic hydrocarbons such as toluene or xylene; aliphatic hydrocarbons such as pentane, cyclopentane, hexane, cyclohexane, and heptane; and chlorohydrocarbons such as methylene chloride or chloroform.

Solvents or solvent mixtures having a boiling point or boiling range of up to 120° C. at 0.1 MPa are preferred.

The solvents (L) are preferably aromatic or aliphatic hydrocarbons.

The silicone compositions (S) are preferably divided into two storable components.

Component 1 contains polyorganosiloxane (A), optionally organosiloxane resin (A1) and hydrosilylation catalyst (C). Component 2 contains organosilicon compound (B) and may also further contain polyorganosiloxane (A) and polydiorganosiloxane (E).

If fillers (D) are employed these are preferably present in both components.

To achieve crosslinking the components are mixed and; crosslinked, preferably by heating, preferably at 20° C. to 250° C., in particular at 100° C. to 150° C.

The silicone gels obtained from the silicone compositions (S) by crosslinking are preferably used in medical applications, for example as wound adhesives or skin adhesives, or in the field of electronics, for example as potting compounds and in display applications, for example as an optically clear adhesive.

All abovementioned symbols in the abovementioned formulae each have their definitions independently of one another. The silicon atom is tetravalent in all formulae.

In the examples which follow, unless otherwise stated, all amounts and percentages are based on weight, all pressures are 101.3 kPa (abs.) and all temperatures are 20° C.

Procedure for Producing the Gels:

The gels are produced by mixing the individual components in a suitable apparatus at room temperature. The crosslinking is generally performed at a temperature of 120° C. over a period of 15 minutes during storage in a forced circulation drying cabinet but may also be performed at room temperature.

Test Methods:

Molecular Compositions:

The molecular compositions are determined by means of nuclear magnetic resonance spectroscopy (regarding terminology see ASTM E 386: high-resolution nuclear magnetic resonance spectroscopy (NMR): terms and symbols) by measuring the $^1$H nucleus.

Description of $^1$H NMR Measurement

Solvent: $CDCl_3$, 99.8% d

Sample concentration: 50 mg/1 ml $CDCl_3$ in 5 mm NMR tubes

Measurement without addition of TMS, spectral referencing of residual $CHCl_3$ in $CDCl_3$ at 7.24 ppm Spectrometer: Bruker Avance I 500 or Bruker Avance HD 500

Probe head: 5 mm BBO probe head or SMART probe head (Bruker)

Measurement Parameters:

Pulprog=zg30

TD=64 k

NS=64 or 128 (depending on sensitivity of probe head)

SW=20.6 ppm

AQ=3.17 s

D1=5 s

SFO1=500.13 MHz

O1=6.175 ppm

Processing Parameters:

SI=32 k

WDW=EM

LB=0.3 Hz

Depending on the spectrometer type used, individual adjustments of the measurement parameters may be required.

Determination of Viscosity:

Unless otherwise stated, the viscosities are determined on an MCR302 rheometer from Anton Paar, Ostfildern, Germany according to DIN EN ISO 3219 in rotation with a cone-plate measuring system. Measurements are carried out in the Newtonian range of the samples. Where a sample exhibits non-Newtonian behaviour, the shear rate is also reported. Unless otherwise stated, all reported viscosities relate to 25° C. and standard pressure of 1013 mbar.

Penetration Measurement:

The penetration of the material is measured according to DIN EN ISO 2137 on a silicone gel sample of 125 g that has been crosslinked for 60 minutes at 120° C. A 62.5 g hollow cone is used and the measurement period is 60 seconds.

Procedure for Producing the Gels:

For a ready to use formulation the constituents described here are divided into component A: vinyl polymer (A), platinum (C), optionally additives, optionally MQ resin (A1);

component B: crosslinker (B), optionally vinyl polymer (A), optionally H polymer (E), optionally MQ resin (A1).

The gels are produced by mixing the components A and B in a suitable apparatus at room temperature. Unless otherwise stated, the crosslinking takes place at a temperature of 120° C. over a period of 15 minutes in a forced circulation drying cabinet.

Determination of Adhesive Force

Sample Preparation:

component A and B of the formulations are mixed with one another at room temperature.

The as yet uncrosslinked silicone composition is applied to polyurethane film (Epurex®) using a commercially available box section blade coater. The strips have a length of at least 140 mm and a width of 25 mm. The layer thickness of the silicone composition is 0.1 mm.

The samples are subsequently vulcanized for 15 minutes at 120° C. and stored for two hours at room temperature before measurement.

90 Degree Peel Force Measurement:

For the values reported in tables 1 and 2 the measurement is performed on a peel force measuring instrument from Q-Tec (ZPFI.01). Per each measurement, four sample strips are adhesively bonded to a stainless steel plate having a bright annealed surface. The strips are pressed down with a hand roller of 2 kg in weight (four passes, two in each direction, rolling speed: about 200 mm/s).

After a 30 minute waiting time and storage at room temperature the peel force measurement is performed simultaneously on all four strips. To this end the strips are pulled from the steel plate at an angle of 90° at a constant speed of 5 mm per second (+/−0.2 mm per second) and the peel force required therefor is measured.

EXAMPLES

Constituents:

ViPo (I): α,ω-dimethylvinylsiloxy-terminated polydimethylsiloxane having a viscosity of 1000 mPa·s and a vinyl content of 0.12 mmol/g (0.33% by weight).

ViPo (II): α,ω-dimethylvinylsiloxy-terminated polydimethylsiloxane having a viscosity of 100,000 mPa·s and a vinyl content of 0.027 mmol/g (0.07% by weight).

HPo: α,ω-dimethylhydrosiloxy-terminated polydimethylsiloxane having a viscosity of 1000 mPa·s and an SiH content of 0.010% by weight.

Crosslinker 1: dimethylhydrosiloxy-terminated poly(dimethylsiloxy) (methylhydrosiloxy) copolymer having a viscosity of 1360 mPa·s and an average hydrogen content of 0.011% by weight (corresponds on average to 2.4 SiH functions per molecule).

Crosslinker 2: dimethylhydrosiloxy-terminated poly(dimethylsiloxy) (methylhydrosiloxy) copolymer having a viscosity of 9450 mPa·s and an average hydrogen content of 0.006% by weight (corresponds on average to 2.9 SiH functions per molecule).

Crosslinker 3: dimethylhydrosiloxy-terminated poly(dimethylsiloxy) (methylhydrosiloxy) copolymer having a viscosity of 1350 mPa·s and an average hydrogen content of 0.014% by weight (corresponds on average to 2.9 SiH functions per molecule).

Crosslinker 4: dimethylhydrosiloxy-terminated poly(dimethylsiloxy) (methylhydrosiloxy) copolymer having a viscosity of 1330 mPa·s and an average hydrogen content of 0.015% by weight (corresponds on average to 3.2 SiH functions per molecule).

Crosslinker 5: dimethylhydrosiloxy-terminated poly(dimethylsiloxy) (methylhydrosiloxy) copolymer having a viscosity of 160 mPa·s and an average hydrogen content of 0.17% by weight (corresponds on average to 11.7 SiH functions per molecule).

Crosslinker 6: trimethylsiloxy-terminated poly(dimethylsiloxy) (methylhydrosiloxy) copolymer having a viscosity of 177 mPa·s and an average hydrogen content of 0.22% by weight (corresponds on average to 16 SiH functions per molecule).

Crosslinker 7: trimethylsiloxy-terminated poly(dimethylsiloxy) (methylhydrosiloxy) copolymer having a viscosity of 94 mPa·s and an average hydrogen content of 0.46% by weight (corresponds on average to 24.0 SiH functions per molecule).

Resin: $Me_3SiO_{1/2}/Me_2ViSiO_{1/2}/SiO_{4/2}$ (Vi-substituted MQ resin), average molecular weight Mn=2100 g/mol, 1.95% by weight vinyl, SiOH content=0.5% by weight Catalyst: platinum-1,3-divinyl-1,1,3,3-tetramethyldisiloxane complex

INVENTIVE EXAMPLES

Example 1

82.90% ViPo (II)
6.25% HPo
0.70% resin
9.50% crosslinker 1
Catalyst corresponds to 6 ppm based on platinum

Example 2

78.50% ViPo (II)
6.50% HPo
0.70% resin
13.60% crosslinker 2

Example 3

89.21% ViPo(II)
5.30% HPo
5.30% crosslinker 3
Catalyst corresponds to 6 ppm based on platinum

Example 4

85.90% ViPo(II)
3.00% resin
11.00% crosslinker 3
Catalyst corresponds to 6 ppm based on platinum

Example 5

91.00% ViPo(II)
0.75% resin
8.15% crosslinker 4
Catalyst corresponds to 6 ppm based on platinum

Example 6

55.48% ViPo (I)
19.28% ViPo (II)
5.50% resin
27.35% crosslinker 4
Catalyst corresponds to 6 ppm based on platinum

Example 7

85.30% ViPo (II)
6.50% HPo
0.70% resin
7.50% crosslinker 4
Catalyst corresponds to 6 ppm based on platinum

TABLE 1

| | Adhesion properties of obtained gels on steel: | | | | | | |
|---|---|---|---|---|---|---|---|
| | Example | | | | | | |
| | 1 | 2 | 3 | 4 | 5 | 6 | 7 |
| Peel force in cN/cm | 157 | 184 | 162 | 178 | 186 | 157 | 160 |
| Nature of tear | adhesive | adhesive | adhesive | adhesive | adhesive | adhesive | adhesive |
| Penetration (1/10 mm) | 156 | 165 | 187 | 209 | 209 | 168 | 151 |
| SiH per crosslinker molecule | 2.4 | 2.9 | 2.9 | 2.9 | 3.2 | 3.2 | 3.2 |
| % by weight of SiH per crosslinker molecule | 0.011 | 0.006 | 0.014 | 0.014 | 0.015 | 0.015 | 0.015 |
| Length of crosslinker molecule | 292 | 645 | 282 | 282 | 286 | 286 | 286 |

NONINVENTIVE EXAMPLES

Example N1

91.40% ViPo(II)
7.40% HPo
0.75% resin
0.45% crosslinker 5
catalyst corresponds to 6 ppm based on platinum

Example N2

91.49% ViPo(II)
7.42% HPo
0.75% resin
0.345% crosslinker 6
catalyst corresponds to 6 ppm based on platinum

Example N3

91.63% ViPo(II)
7.45% HPo
0.75% resin
0.175% crosslinker 7
catalyst corresponds to 6 ppm based on platinum

TABLE 2

Adhesion properties of obtained non-inventive gels on steel and comparison with inventive examples 1 and 7:

| | Example | | | | |
|---|---|---|---|---|---|
| | 1 | 7 | N1* | N2* | N3* |
| Detachment force in cN/cm | 157 | 160 | 64 | 66 | 23 |
| Nature of tear | adhesive | adhesive | adhesive | adhesive | adhesive |
| Penetration in ¹⁄₁₀ mm | 156 | 151 | 146 | 149 | 138 |
| SiH units per crosslinker moleule | 2.4 | 3.2 | 11.7 | 15.9 | 24.0 |
| % by weight of SiH per crosslinker molecule | 0.011 | 0.015 | 0.166 | 0.220 | 0.46 |
| Total SiH content of formulation [ppm] | 3340 | 3380 | 3099 | 3133 | 2391 |

*non inventive

The invention claimed is:

1. A silicone composition crosslinkable to provide a silicone gel, comprising:
   (A) at least one polyorganosiloxane containing at least two alkenyl groups per molecule, and having a viscosity at 25° C. of 200 to 500,000 mPa·s measured according to DIN EN ISO 3219 in rotation with a cone-plate measuring system at 1013 mbar,
   (B) at least one organosilicon compound containing at least two SiH groups per molecule and having an average content of 2.5 to 3.5 SiH groups per molecule and a content of not more than 0.025% by weight of SiH group hydrogen,
   and
   (C) a hydrosilylation catalyst,
   wherein a portion of polyorganosiloxane (A) is an organosiloxane resin (A1) comprising units of formulae I, II, III and IV $$R_3SiO_{1/2} \quad (I),$$

$$R_2SiO_{2/2} \quad (II),$$

$$RSiO_{3/2} \quad (III),$$

$$SiO_{4/2} \quad (IV),$$

in which
   R is $R^1$, $R^2$ or OH,
   wherein
   $R^1$ is a monovalent, unsubstituted or halogen- or cyano-substituted, $C_1$-$C_{10}$-hydrocarbon radical optionally bonded to silicon via an organic divalent group and containing at least one aliphatic carbon-carbon multiple bond,
   $R^2$ is a monovalent, unsubstituted or halogen- or cyano-substituted, SiC-bonded $C_1$-$C_{10}$-hydrocarbon radical free from aliphatic carbon-carbon multiple bonds,
   with the proviso that
   at least 20 mol % of the units are units of formulae III and IV,
   at least 2 of the radicals R are radicals $R^1$, and not more than 2% by weight of the radicals R are radicals OH.

2. A silicone composition crosslinkable to provide a silicone gel, comprising:
   (A) at least one polyorganosiloxane containing at least two alkenyl groups per molecule, and having a viscosity at 25° C. of 200 to 500,000 mPa·s measured according to DIN EN ISO 3219 in rotation with a cone-plate measuring system at 1013 mbar,
   (B) at least one organosilicon compound containing at least two SiH groups per molecule and having an average content of 2.5 to 3.5 SiH groups per molecule and a content of not more than 0.025% by weight of SiH group hydrogen,
   and
   (C) a hydrosilylation catalyst,
   wherein the alkenyl-containing polyorganosiloxane (A) comprises units of formula (1)

$$R^1_x R^2_y SiO_{(4-x-y)/2} \quad (1),$$

in which
   $R^1$ is a monovalent, unsubstituted or halogen- or cyano-substituted, $C_1$-$C_{10}$-hydrocarbon radical optionally bonded to silicon via an organic divalent group and containing at least one aliphatic carbon-carbon multiple bond,
   $R^2$ is a monovalent, unsubstituted or halogen- or cyano-substituted, SiC-bonded $C_1$-$C_{10}$-hydrocarbon radical free from aliphatic carbon-carbon multiple bonds,
   x is 0, 1 or 2,
   y is 0, 1, 2 or 3,
   with the proviso that at least two radicals $R^1$ are present in each molecule and the average value of (x+y) is in the range from 1.8 to 2.5, and
   wherein a portion of polyorganosiloxane (A) is an organosiloxane resin (A1) comprising units of formulae I, II, III and IV $$R_3SiO_{1/2} \quad (I),$$

$$R_2SiO_{2/2} \quad (II),$$

$$RSiO_{3/2} \quad (III),$$

$$SiO_{4/2} \quad (IV),$$

in which
   R is $R^1$, $R^2$ or OH,
   wherein
   $R^1$ is a monovalent, unsubstituted or halogen- or cyano-substituted, $C_1$-$C_{10}$-hydrocarbon radical optionally bonded to silicon via an organic divalent group and containing at least one aliphatic carbon-carbon multiple bond,
   $R^2$ is a monovalent, unsubstituted or halogen- or cyano-substituted, SiC-bonded $C_1$-$C_{10}$-hydrocarbon radical free from aliphatic carbon-carbon multiple bonds,
   with the proviso that
   at least 20 mol % of the units are units of formulae III and IV,
   at least 2 of the radicals R are radicals $R^1$, and not more than 2% by weight of the radicals R are radicals OH.

3. A silicone composition crosslinkable to provide a silicone gel, comprising:
   (A) at least one polyorganosiloxane containing at least two alkenyl groups per molecule, and having a viscosity at 25° C. of 200 to 500,000 mPa·s measured according to DIN EN ISO 3219 in rotation with a cone-plate measuring system at 1013 mbar,
   (B) at least one organosilicon compound containing at least two SiH groups per molecule and having an average content of 2.5 to 3.5 SiH groups per molecule and a content of not more than 0.025% by weight of SiH group hydrogen,
and
(C) a hydrosilylation catalyst,
wherein the alkenyl-containing polyorganosiloxane (A) contains vinyl-containing polydimethylsiloxanes of formula (3)

$$(ViMe_2SiO_{1/2})_2(ViMeSiO)_p(Me_2SiO)_q \qquad (3),$$

wherein
Vi is a vinyl radical and
Me is a methyl radical
and the non-negative integers p and q conform to the following relations: $p \geq 0$, $50 < (p+q) < 20{,}000$ and $0 < (p+1)/(p+q) < 0.2$, and
wherein a portion of polyorganosiloxane (A) is an organosiloxane resin (A1) comprising units of formulae I, II, III and IV $$R_3SiO_{1/2} \qquad (I),$$

$$R_2SiO_{2/2} \qquad (II),$$

$$RSiO_{3/2} \qquad (III),$$

$$SiO_{4/2} \qquad (IV),$$

in which
R is $R^1$, $R^2$ or OH,
wherein
$R^1$ is a monovalent, unsubstituted or halogen- or cyano-substituted, $C_1$-$C_{10}$-hydrocarbon radical optionally bonded to silicon via an organic divalent group and containing at least one aliphatic carbon-carbon multiple bond,
$R^2$ is a monovalent, unsubstituted or halogen- or cyano-substituted, SiC-bonded $C_1$-$C_{10}$-hydrocarbon radical free from aliphatic carbon-carbon multiple bonds,
with the proviso that
at least 20 mol % of the units are units of formulae III and IV,
at least 2 of the radicals R are radicals $R^1$, and not more than 2% by weight of the radicals R are radicals OH.

4. The silicone composition of claim 2, wherein the organosilicon compound (B) containing at least two SiH functions per molecule comprises units of formula (4)

$$H_aR^3{}_bSiO_{(4-a-b)/2} \qquad (4),$$

in which
$R^3$ is a monovalent, unsubstituted or halogen- or cyano-substituted, SiC-bonded $C_1$-$C_{18}$-hydrocarbon radical free from aliphatic carbon-carbon multiple bonds,
a is 0, 1, or 2,
b is 0, 1, 2 or 3, and
with the proviso that at least two silicon-bonded hydrogen atoms per molecule are present.

5. The silicone composition of claim 3, wherein the organosilicon compound (B) containing at least two SiH functions per molecule comprises units of formula (4)

$$H_aR^3{}_bSiO_{(4-a-b)/2} \qquad (4),$$

in which
$R^3$ is a monovalent, unsubstituted or halogen- or cyano-substituted, SiC-bonded $C_1$-$C_{18}$-hydrocarbon radical free from aliphatic carbon-carbon multiple bonds,
a is 0, 1, or 2,
b is 0, 1, 2 or 3, and
with the proviso that at least two silicon-bonded hydrogen atoms per molecule are present.

6. The silicone composition of claim 1, wherein the organosilicon compound (B) containing at least two SiH functions per molecule comprises units of formula (4)

$$H_aR^3{}_bSiO_{(4-a-b)/2} \qquad (4),$$

in which
$R^3$ is a monovalent, unsubstituted or halogen- or cyano-substituted, SiC-bonded hydrocarbon radical free from aliphatic carbon-carbon multiple bonds,
a is 0, 1, or 2,
b is 0, 1, 2 or 3, and
with the proviso that at least two silicon-bonded hydrogen atoms per molecule are present.

7. The silicone composition of claim 1, wherein the organosilicon compound (B) contains 50 to 1000 silicon atoms per molecule.

8. The silicone composition of claim 1, wherein the organosilicon compound (B) contains at least one linear polyorganosiloxane of formula (5)

$$(HR^4{}_2SiO_{1/2})_c(R^4{}_3SiO_{1/2})_d(HR^4SiO_{2/2})_e(R^4{}_2SiO_{2/2})_f \qquad (5),$$

wherein
$R^4$ is a monovalent, unsubstituted or halogen- or cyano-substituted, SiC-bonded $C_1$-$C_{18}$-hydrocarbon radical free from aliphatic carbon-carbon multiple bonds, and
the non-negative integers c, d, e and f fulfill the following relations: $(c+d)=2$, $(c+e) \geq 2$ and $50 < (e+f) < 1000$.

9. The silicone composition of claim 1, which further comprises a linear polydiorganosiloxane (E) whose two chain ends each bear an SiH group and whose chain is free from SiH groups.

10. A skin adhesive or wound adhesive, comprising a crosslinked composition of claim 1.

* * * * *